United States Patent [19]

Moore

[11] Patent Number: 5,173,123
[45] Date of Patent: Dec. 22, 1992

[54] METHOD FOR FREEING OBSTRUCTIONS FORMED IN A HOLLOW SURGICAL SUCTION IMPLEMENT

[76] Inventor: Jerry L. Moore, 6229 N. Lafayette St., Fresno, Calif. 93711

[21] Appl. No.: 755,447

[22] Filed: Sep. 5, 1991

Related U.S. Application Data

[62] Division of Ser. No. 620,712, Dec. 3, 1990, Pat. No. 5,115,532.

[51] Int. Cl.$^5$ ............................. B08B 5/04; B08B 9/00
[52] U.S. Cl. ......................................... 134/8; 134/2.1; 134/22.11
[58] Field of Search ............. 134/8, 21, 22.11, 104.92, 134/160, 159 A

[56] References Cited

U.S. PATENT DOCUMENTS

| | | | |
|---|---|---|---|
| 116,272 | 7/1938 | McKeen | 362/375 |
| 619,257 | 2/1899 | Judd | 239/288.5 |
| 2,090,326 | 8/1932 | Glatitice | 239/103 |
| 2,899,929 | 11/1957 | Monroe | 118/302 |
| 3,956,011 | 5/1976 | Carleton | 134/21 |
| 4,087,878 | 5/1978 | Grieshaber et al. | 15/111 |
| 4,362,572 | 12/1982 | Wallace | 134/21 |
| 4,439,884 | 2/1984 | Giorni | 15/104.92 |
| 4,486,238 | 12/1984 | Bando | 134/21 |
| 4,547,923 | 10/1985 | Devries et al. | 15/104 R |
| 4,600,444 | 7/1986 | Miner | 134/22.11 |
| 4,683,603 | 8/1987 | Purlia et al. | 15/104.92 |
| 4,872,235 | 10/1989 | Nielsen | 15/104.92 |
| 4,890,348 | 1/1990 | Racioppi | 15/160 |

Primary Examiner—Theodore Morris
Assistant Examiner—Saeed T. Chaudhry
Attorney, Agent, or Firm—Shlesinger, Arkwright & Garvey

[57] ABSTRACT

A preferred embodiment is directed to a system for freeing obstructions formed in a hollow surgical suction implement having first and second open ends. The system includes a fluid container having at least one opening for receiving the first open end of the hollow surgical suction implement. A plurality of bristles are formed in the fluid container. The bristles are tapered to facilitate insertion in the hollow surgical suction implement and provide greater stability. Level identifying indicia is formed on the fluid container to identify the amount of fluid therein. A vacuum suction system is adapted to be operably connected to the second open end of the hollow surgical suction implement to direct fluid in the fluid container through the surgical suction implement at a predetermined time after the first end of the surgical suction implement is inserted in the fluid container. The vacuum suction system directs fluid passing therethrough into a reservoir. The reservoir includes level identifying indicia for identifying the level of fluid therein.

4 Claims, 3 Drawing Sheets

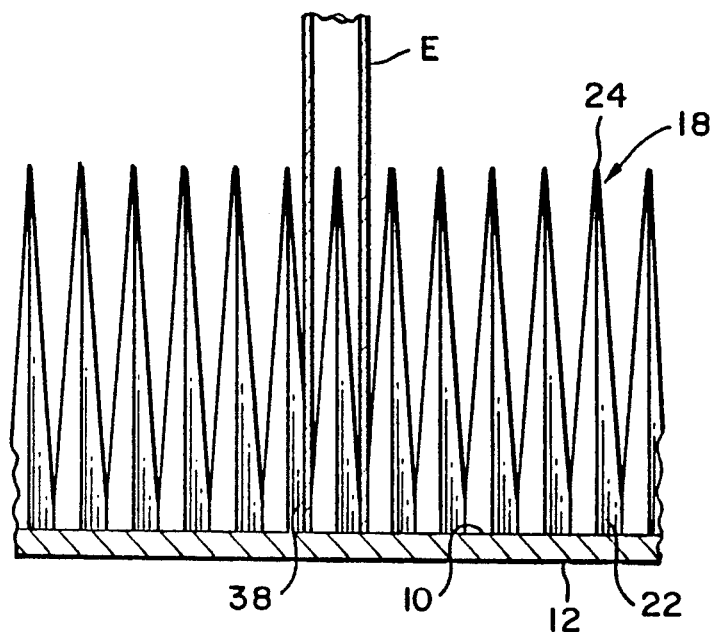
FIG_3
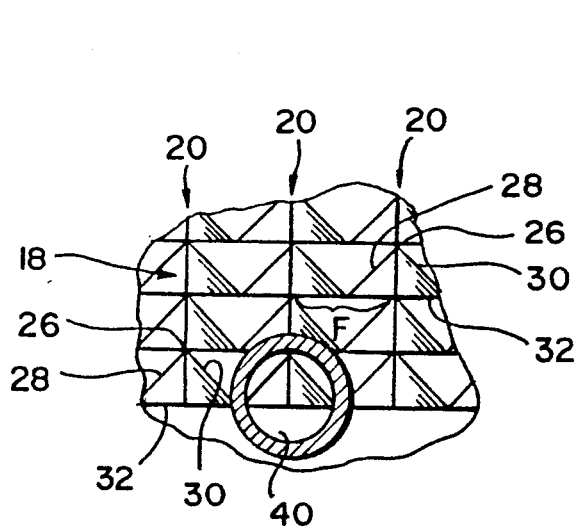
FIG_4
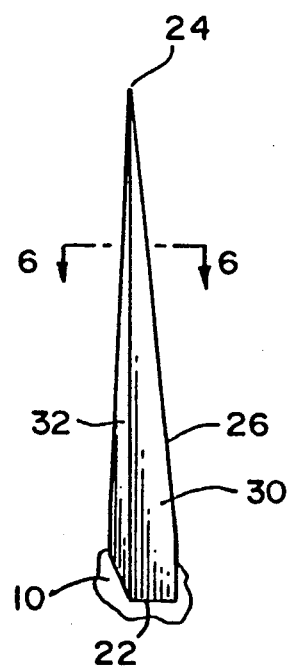
FIG_5
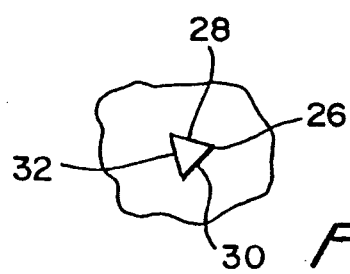
FIG_6

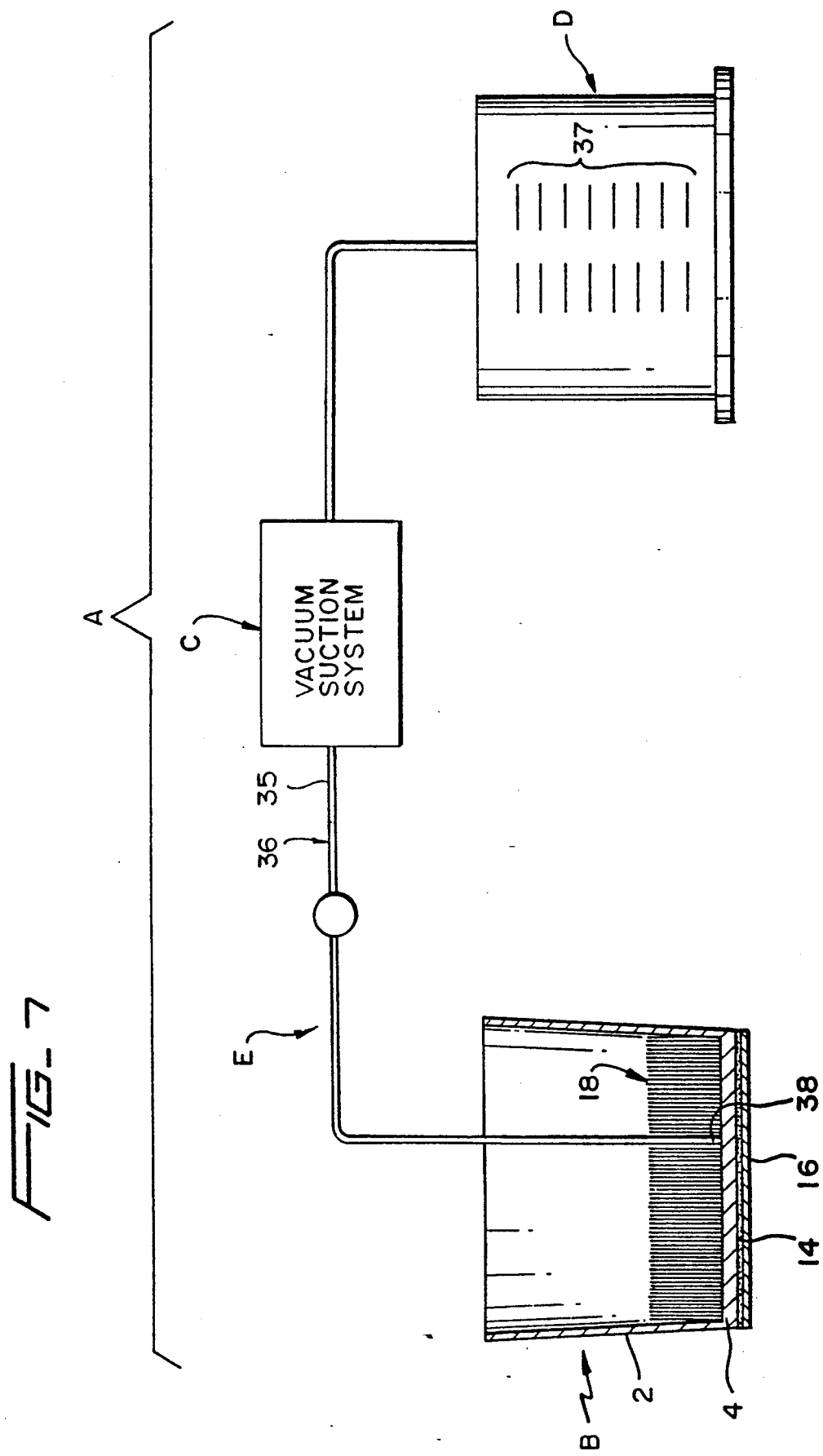

METHOD FOR FREEING OBSTRUCTIONS FORMED IN A HOLLOW SURGICAL SUCTION IMPLEMENT

This is a division of application Ser. No. 07/620,712 filed Dec. 3, 1990, now U.S. Pat. No. 5,115,532.

FIELD OF THE INVENTION

The present invention is directed to an apparatus and method for clearing obstructions formed in surgical suction implements.

BACKGROUND OF THE INVENTION

Microsurgery is a specialized procedure for operating on microscopic objects through the use of a surgical microscope. A microsuction, tip unit is used to aspirate blood from and around the incision during microsurgery. The microsuction tip unit includes a microsuction tip, which is an extremely small and hollow surgical implement, and a vacuum suction system. The vacuum suction system is connected at one end to the microsuction tip and channels blood therethrough. The suctioned blood is collected in a reservoir.

During surgery the microsuction tip often becomes clogged with blood clots, bone fragments and the like. Previously known techniques for freeing obstructions required the surgeon to stop the surgical procedure and hand the microsuction tip to a nurse who would free the obstruction. Conventionally, nurses have used a long, thin, hair-like instrument known as an obturator to free the obstructions. Specifically, the nurse was required to insert the obturator into the extremely small opening at the end of the microsuction tip to free the obstruction. This process requires the use of two hands and a great degree of dexterity. Further, it is extremely tedious and time consuming, thereby increasing the risk to the patient.

OBJECTS AND SUMMARY OF THE INVENTION

An object of the present invention is to provide an improved apparatus and method for freeing obstructions formed in hollow surgical suction implements.

Another object of the present invention is to provide an apparatus for freeing obstructions formed in a hollow surgical suction implement having first and second open ends which includes fluid container means for containing a fluid therein. An opening is formed in the fluid container means for receiving a first open end of a hollow surgical suction implement. The fluid container means further includes interior and exterior surfaces. A plurality of bristles are disposed in the fluid container means. At least one of the plurality of bristles has a first end secured to the interior surface and a second end removed therefrom. Indicating means are formed on at least one of the interior and exterior surfaces for indicating fluid level in the fluid container means. An apparatus formed in a manner recited above is advantageous, for among other reasons, because a surgeon using the same can readily and reliably keep track of the amount of blood suctioned from the patient during the operation and also clean the blockage.

A further object of the present invention is to provide an apparatus for freeing obstructions formed in a hollow surgical suction implement having first and second open ends which includes fluid container means for containing a fluid therein. At least one opening is formed in the fluid container means for receiving one end of a hollow surgical suction implement. The fluid container means further includes interior and exterior surfaces. A plurality of bristles are disposed in the fluid container means. At least one of the plurality of bristles has a first end secured to the interior surface of the fluid container means and a second end removed therefrom. At least a portion of the at least one of the plurality of bristles intermediate the first and second ends is tapered. This configuration is desirable for a number of reasons, several of which are enumerated below. By tapering a portion of the bristle intermediate the first and second ends thereof, the bristle can be readily and easily inserted into the hollow surgical suction implement to free any obstructions formed therein. Further, the tapered arrangement provides the bristle with greater stability, thereby reducing the likelihood of the bristle bending over rather than entering the open end of the hollow surgical suction implement upon application of a force thereto.

Still a further object of the present invention is to provide a system for freeing obstructions formed in a hollow surgical suction implement having first and second open ends which includes fluid container means for containing a fluid therein. The fluid container means includes at least one opening for receiving a first open end of a hollow surgical suction implement. The fluid container means further includes interior and exterior surfaces. A plurality of bristles are disposed in the fluid container means. A vacuum suction means is adapted to be operably connected to a second open end of the hollow surgical suction implement for directing fluid in the fluid container means through the surgical suction implement at a predetermined time after the first end of the surgical suction implement is inserted in the fluid container means. The system recited above is desirable, for among other reasons, in that it is designed to permit fluid to flow through the hollow surgical suction implement once the obstruction is freed. The fluid forces the obstructing material through the hollow surgical suction implement and thereby significantly reduces the likelihood of further blockages forming upstream of the initial blockage.

Yet still another object of the present invention is to provide a method of freeing obstructions formed in a hollow surgical suction implement having first and second open ends including the steps of providing a fluid container means for containing a fluid therein, the fluid container means having a base and a plurality of bristles formed therein; providing a fluid in the fluid container; providing a hollow surgical suction implement having first and second open ends; inserting the first end of the hollow surgical suction implement into the fluid container means such that at least one of the bristles extends into the hollow cavity to free any obstructions lodged therein; and, directing at least a portion of the fluid in the fluid container means through the suction implement to carry obstructions freed by the bristles therethrough. The above method of freeing obstructions formed in a hollow surgical suction implement is a significant improvement over previously known methods. For example, the surgeon need only insert the first end of a hollow surgical suction implement into the container so that one or more bristles extend into the hollow cavity to free blockages therein. This obviates the need for performing the difficult and time consuming task of threading an obturator through the tiny opening in a microsuction tip. Further, by directing fluid through the hollow surgical suction implement the material causing the blockage is readily passed therethrough.

These objects and advantages as well as others will be readily apparent from a review of the detailed description of the invention, the drawings and the attached claims.

In summary, a preferred embodiment of the present invention is directed to a system for freeing obstructions formed in a hollow surgical suction implement having first and second open ends. The system includes a fluid container having at least one opening for receiving the first open end of the hollow surgical suction implement. A plurality of bristles are formed in the fluid container. The bristles are tapered to facilitate insertion in the hollow surgical suction implement and provide greater stability. Level identifying indicia is formed on the fluid container to identify the amount of fluid therein. A vacuum suction system is adapted to be operably connected to the second open end of the hollow surgical suction implement to direct fluid in the fluid container through the surgical suction implement at a predetermined time after the first end of the surgical suction implement is inserted in the fluid container. The vacuum suction system directs fluid passing therethrough into a reservoir. The reservoir includes level identifying indicia for identifying the level of fluid therein.

DETAILED DESCRIPTION OF THE DRAWINGS

FIG. 3 is an enlarged fragmentary cross sectional view of a portion of the fluid container formed in accordance with the preferred embodiment of the present invention.

FIG. 4 is an enlarged fragmentary plan view of the embodiment illustrated in FIG. 1.

FIG. 5 is a perspective view of a single bristle which is disposed in the fluid container illustrated in FIG. 1.

FIG. 6 is a cross-sectional view taken along lines 6—6 in FIG. 5.

FIG. 7 illustrates a system for freeing obstructions formed in a hollow surgical suction implement formed in accordance with the preferred embodiment of the present invention.

DETAILED DESCRIPTION OF THE INVENTION

The preferred embodiment of the present invention will be described hereinafter with reference made to FIGS. 1 through 7.

Figure 1:
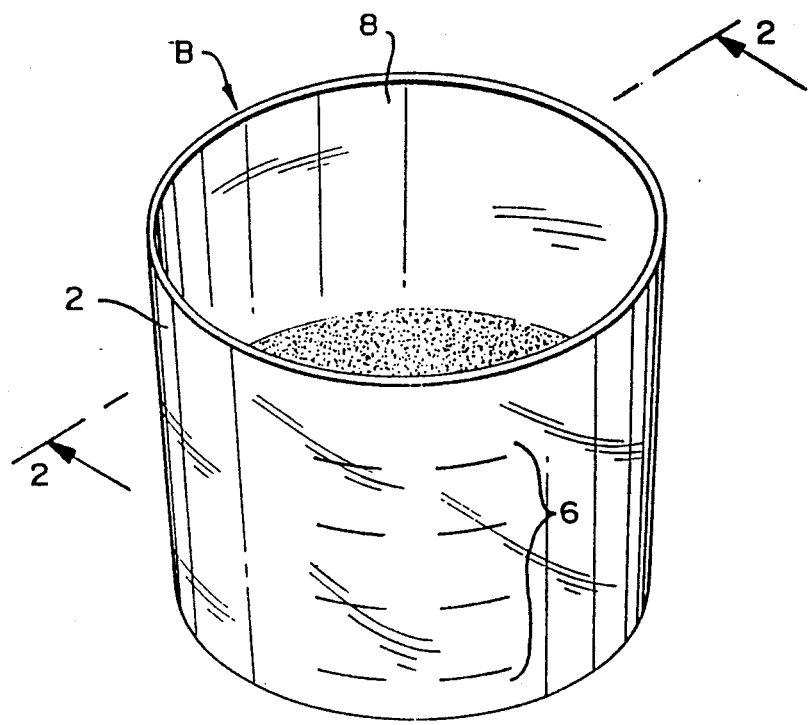
FIG. 1 is a perspective view of a fluid container formed in accordance with the preferred embodiment of the present invention.
Figure 2:
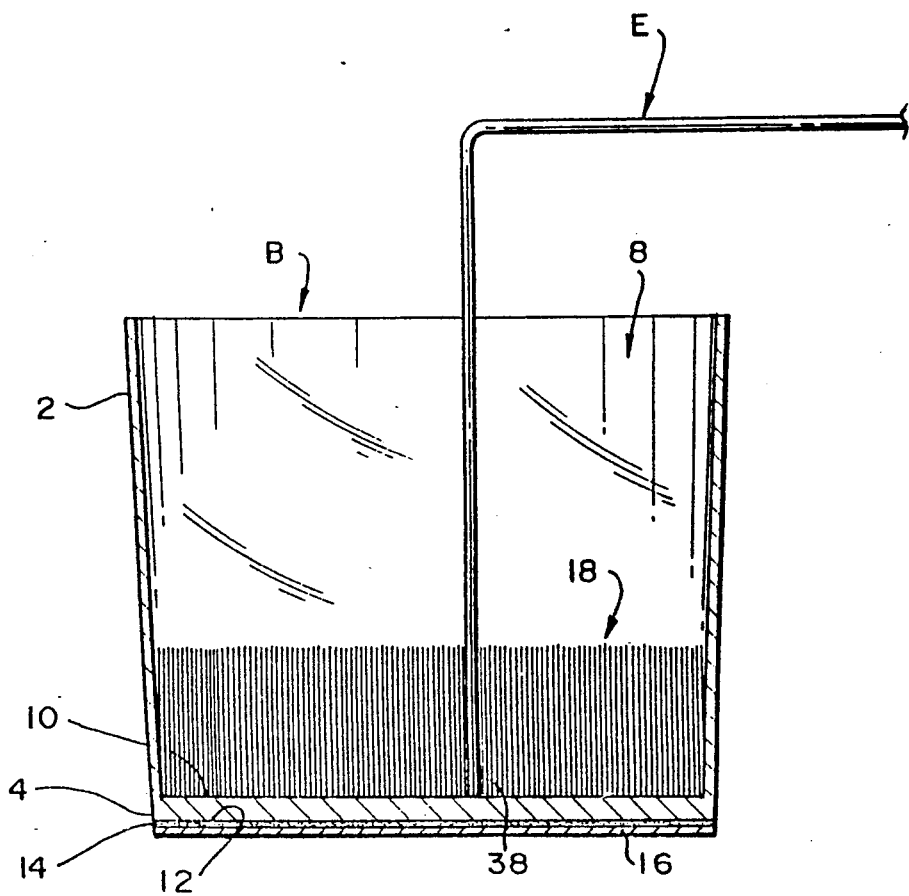
FIG. 2 is a cross-sectional view taken along lines 2—2 in FIG. 1 and further depicts a microsuction tip inserted therein.

Referring to FIG. 7, an obstruction freeing system A includes a fluid container B, a vacuum suction system C and a reservoir D. The vacuum suction system C is connected at one end to microsuction tip E. As seen in FIGS. 1 and 2, fluid container B includes a retaining wall 2 and a base 4. Preferably, the retaining wall 2 is formed from a transparent material so that an individual can readily examine the contents of fluid container B. Level identifying indicia 6 are formed on the exterior surface of retaining wall 2 to indicate the level of fluid in the fluid container B. It will be readily appreciated that indicia 6 can take the form of any known unit of measurement for fluids. An opening 8 is formed in the upper surface of fluid container B.

Referring to FIG. 2, base 4 includes an upper surface 10 and a lower surface 12. Preferably, an adhesive material 14 is applied to substantially the entire lower surface 12 of base 4. A protective sheet 16 is releasably secured to the adhesive material 14. Upon removal of the protective sheet 16, the fluid container B may be readily secured to a support platform via adhesive material 14. A plurality of bristles 18 are secured to and extend upwardly from upper surface 10 of base 4. The bristles 18 are formed integral with base 4. However, bristles 18 may be formed on a supporting layer which is removably secured to base 4.

The details concerning the arrangement of bristles 18 in fluid container B will be explained with reference made to FIGS. 3 through 5. As seen in FIG. 4, bristles 18 are arranged in a plurality of rows 20. Each bristle 18 includes a bottom 22 secured to the lower surface 10 and an apex 24 removed therefrom, as best seen in FIG. 5. Bristles 18 further include front edge 26, left side 28, right side 30 and rear face 32. The left side 28 and right side 30 each form an acute angle with the rear face 32. Further the left and right sides 28 and 30 extend forwardly from rear face 32 to front edge 26. Thus, as seen in FIG. 6, bristles 18 have a substantially triangularly-shaped cross-section. However, it will be readily understood that bristles 18 may be provided with any cross-section which differs from the cross-section of the hollow surgical suction tip E. The bristles 18 are tapered from an area just above the bottom 22 to the tip 24.

Rows 20 are arranged such that the rear surfaces 32 extend substantially parallel to each other. The left sides 28 of each of the bristles 18 extend substantially parallel to each other. Similarly, the right sides 30 of each of the bristles 18 extend substantially parallel to each other. Further, in each of the rows 20, the bristles 18 are positioned such that the front edges 26 are substantially aligned on a common axis. It will be readily appreciated that the number of bristles 18 in the rows 20 will diminish as you move outwardly from the center of fluid container B.

In the preferred embodiment, the distance F between the midsection of rear faces 32 of adjacent bristles 18 is approximately 3/64 of an inch. Preferably, the container B is formed from a low density polyethylene plastic by injection molding.

The vacuum suction system C shown in FIG. 7 is of conventional construction and, therefore, it will not be described in detail hereinafter. The rearwardmost open end 36 of microsuction tip E is connected to a flexible hose 35 extending from the vacuum suction system C. The vacuum suction system C drains into reservoir D. The reservoir D is preferably formed from a transparent material and includes level identifying indicia 37 formed on the exterior surface thereof. The level identifying indicia 37 can be expressed in any known unit of measurement for fluids.

METHOD OF FREEING OBSTRUCTIONS FORMED IN A HOLLOW SURGICAL SUCTION IMPLEMENT

The preferred method of freeing obstructions from a hollow surgical suction implement will be described hereinafter with reference made to FIGS. 2 through 7.

During microsurgery, the forwardmost open end 38 of microsuction tip E, which preferably has a diameter substantially equal to the width of rear face 32, is positioned in or around the incision to aspirate blood therefrom. The blood is drained into the reservoir D via vacuum suction system C. However, the open end 38 of microsuction tip E often becomes clogged with blood clots, bone fragments and the like thereby preventing the microsuction tip E from aspirating additional blood from and around the incision. This is largely due to the fact that the portion of the microsuction tip E immediately adjacent open end 38 is the narrowest section thereof.

To free any blockage in the area around open end 38, the instrument E is merely inserted into the fluid container B such that at least one of the bristles 18 extends into the hollow cavity 40, as seen in FIG. 4. Although FIG. 4 illustrates only one bristle entering the hollow instrument E, it will be readily appreciated that the size of bristles 18 may be varied such that more than one can be inserted therein. Once the obstruction is freed, the vacuum suction system will draw the obstructing material and fluid contained in fluid container B through microsuction tip E. The triangular cross-section of bristles 18, which differs from the circular cross-section of the open end 38, permits the fluid in the container B to be drawn up into the hollow cavity 40 of implement E. The positioning of the bristles 18, as shown in FIG. 4, helps to further ensure that fluid is permitted to pass through the microsuction tip E even when more than one bristle 18 is inserted in open end 38 thereof. The fluid from fluid container B assists the obstructing material through the microsuction tip E and prevents further blockages from forming upstream of the initial blockage, and may include water, a saline solution or other cleaning composition.

The tapered design of bristles 18 facilitates their insertion into open end 38 of microsuction tip E. Further, the tapered configuration provides the bristles 18 with greater stability than bristles formed with a uniform cross-section of the size of apex 24. Thus, bristles 18 are less likely to bend over rather than enter the open end 38 when a force is applied thereto, particularly a force not aligned directly with the vertical axis of bristles 18.

A further aspect of the present invention will now be discussed with reference made to FIG. 7. During some surgical procedures, it is important to monitor the amount of blood aspirated from and around the incision. The level identifying indicia 37 permits a surgeon or other medical personnel to readily determine the amount of fluid which is deposited in reservoir D. However, the fluid deposited in reservoir D includes the patient's blood and any fluid from container B suctioned through the implement E when clearing blockages therefrom. Unless the fluid from container B is accounted for, an erroneous value will be obtained for the blood suctioned from the patient. The level identifying indicia 6 of fluid container B permits the attending medical personnel to readily determine the amount of fluid in container B which is drawn through the microsuction tip E and deposited in reservoir D. Therefore, by subtracting the amount of fluid drawn from container B from the level of fluid in reservoir D, the attending medical personnel are able to obtain an accurate valve of blood suctioned from the patient during surgery.

While this invention has been described as having a preferred design, it is understood that it is capable of further modifications, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

I claim:

1. A method of freeing obstructions formed in a hollow surgical suction implement having first and second open ends, comprising the steps of:
   a) providing a fluid container having a plurality of bristles formed therein;
   b) providing a fluid in the fluid container;
   c) providing a hollow surgical suction implement having first and second open ends;
   d) inserting the first end of the hollow surgical suction implement into the fluid container such that at least one of the bristles extends into the hollow cavity to free any obstructions therein;
   e) connecting a suction member to the second end of the hollow surgical suction implement for directing at least a portion of the fluid in the fluid container into the first end and out through the second end of the hollow surgical suction implement to carry obstructions freed by the bristles therethrough; and,
   f) directing at least a portion of the fluid in the fluid container through the hollow surgical suction implement to carry obstructions freed by at least one bristle therethrough.

2. A method as in claim 1, including the further step of:
   a) connecting vacuum suction means to the second end of the hollow surgical suction implement for directing at least a portion of the fluid in the fluid container means into the first end and out through the second end of the hollow surgical suction implement to carry obstructions freed by the bristles therethrough.

3. A method as in claim 1, including the further step of:
   a) providing a reservoir operably connected to the vacuum suction means, the reservoir having indicating means formed thereon for determining a level of fluid therein.

4. A method of freeing obstructions formed in a hollow surgical suction implement having first and second open ends, comprising the steps of:
   a) providing a fluid container having a plurality of bristles formed therein and a level indicator indicating the level of fluid contained in the fluid container;
   b) providing a fluid in the fluid container;
   c) providing a hollow surgical suction implement having first and second open ends;
   d) inserting the first end of the hollow surgical suction implement into the fluid container means such that at least a portion of one of the bristles extends into the hollow cavity to free any obstructions therein;
   d) connecting a vacuum suction member to the second end of the hollow surgical implement for directing at least a portion of the fluid in the fluid container into the first and end and out through the second end of the hollow surgical suction implement to carry obstructions freed by the bristles therethrough; and,
   f) directing at least a portion of the fluid in the fluid container through the hollow surgical suction implement to carry obstructions freed by at least one bristle therethrough.

* * * * *